United States Patent
Lou et al.

(10) Patent No.: US 10,169,888 B2
(45) Date of Patent: Jan. 1, 2019

(54) BACKGROUND CORRECTION FOR COMPUTED TOMOGRAPHY SCAN DATA

(71) Applicant: SHENYANG NEUSOFT MEDICAL SYSTEMS CO., LTD., Shenyang (CN)

(72) Inventors: Shanshan Lou, Shenyang (CN); Jiangwei Zhao, Shenyang (CN)

(73) Assignee: Shenyang Neusoft Medical Systems Co., Ltd., Shenyang (CN)

(*) Notice: Subject to any disclaimer, the term of this patent is extended or adjusted under 35 U.S.C. 154(b) by 85 days.

(21) Appl. No.: 15/179,808

(22) Filed: Jun. 10, 2016

(65) Prior Publication Data
US 2017/0169587 A1    Jun. 15, 2017

(30) Foreign Application Priority Data
Dec. 11, 2015  (CN) .......................... 2015 1 0920996

(51) Int. Cl.
| G06T 11/00 | (2006.01) |
| A61B 6/00 | (2006.01) |
| A61B 6/03 | (2006.01) |

(52) U.S. Cl.
CPC ............ *G06T 11/005* (2013.01); *A61B 6/032* (2013.01); *A61B 6/488* (2013.01); *A61B 6/5205* (2013.01); *A61B 6/5258* (2013.01)

(58) Field of Classification Search
None
See application file for complete search history.

(56) References Cited

U.S. PATENT DOCUMENTS

| 4,313,163 A | * | 1/1982 | Mizutani ................ A61B 6/032 378/14 |
| 5,099,505 A | * | 3/1992 | Seppi ..................... A61B 6/032 378/19 |

(Continued)

FOREIGN PATENT DOCUMENTS

| CN | 103679642 A | 3/2014 |
| JP | H01153141 A | 6/1989 |

(Continued)

OTHER PUBLICATIONS

Van Nieuwenhove et al., "Dynamic intensity normalization using eigen flat fields in X-ray imaging," Optics Express. 23 (21): 27975-27989, Oct. 2015.*

(Continued)

*Primary Examiner* — Matthew Bella
*Assistant Examiner* — Soo Shin
(74) *Attorney, Agent, or Firm* — McCoy Russell LLP (57) ABSTRACT

A background correction method for CT scan data is provided. A background collection may be performed to collect a first background data set and background data before a CT scan. The CT scan may then be performed to collect one or more CT scan data sets, and status information for collecting each of the CT scan data sets. A second background collection may additionally be performed to collect a second background data set after the CT scan, and status information for collecting the second background data set may also be recorded. The first background data set, the second background data set and corresponding status information may then be used to obtain a background data set for collecting each of the CT scan data sets. The corresponding background data set may be removed from each of the CT scan data set to obtain a background-corrected CT scan data set.

7 Claims, 3 Drawing Sheets

(56) References Cited

U.S. PATENT DOCUMENTS

| | | | |
|---|---|---|---|
| 5,117,445 A * | 5/1992 | Seppi | A61B 6/032 378/19 |
| 9,763,631 B2 * | 9/2017 | Hefetz | A61B 6/037 |
| 2009/0129657 A1 | 5/2009 | Huo et al. | |
| 2011/0274333 A1 * | 11/2011 | Prevrhal | G06T 11/005 382/132 |
| 2011/0293161 A1 * | 12/2011 | Yi | G06T 11/005 382/131 |
| 2012/0275569 A1 * | 11/2012 | Xue | A61B 6/4233 378/91 |
| 2013/0004052 A1 * | 1/2013 | Chen | G06T 11/005 382/132 |
| 2015/0029178 A1 | 1/2015 | Claus et al. | |
| 2016/0247279 A1 * | 8/2016 | Lavi | G06F 19/3431 |
| 2017/0039734 A1 * | 2/2017 | Langan | G06T 11/003 |

FOREIGN PATENT DOCUMENTS

| | | |
|---|---|---|
| JP | 2008287046 A | 11/2008 |
| KR | 20110019264 A | 2/2011 |

OTHER PUBLICATIONS

Yu Xiao-E, Luo Jun-Fang, Chen Wu-Fan; Ring artifact correction of CT images based on sinogram; Journal of the Fourth Military Medical University, 2009,30(3).

* cited by examiner

BACKGROUND CORRECTION FOR COMPUTED TOMOGRAPHY SCAN DATA

CROSS-REFERENCE TO RELATED APPLICATIONS

The present application claims priority to Chinese Patent Application No. 201510920996.2, filed on Dec. 11, 2015, the entire contents of which are hereby incorporated by reference for all purposes.

BACKGROUND

The present disclosure is directed to background correction for Computed Tomography (CT) scan data.

A CT scan diagnosis process may comprise the steps of: X-rays emitted by a light source irradiating a particular portion of a subject; the X-rays reach a detector after it may be attenuated by the scanned portion; the detector converts the received signal into a digital signal (hereinafter also called "a CT scan data set"); and then a CT image may be reconstructed based on the CT scan data set for medical diagnosis use.

Theoretically, the signal received by the detector ought to simply be the attenuated X-ray signal. However, due to a dark current of a CT detector's photodiodes, a bias current of integrators, and a noise that may exist during a data conversion process, there may typically be an offset in the CT scan data set collected by the detector when comparing with the theoretical X-ray data. This offset may be called "background" or background noise. In practice, the background may be eliminated in order to enhance the quality of the reconstructed CT image.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machines, Ultrasound, Positron Emission Tomography (PET), Linear Accelerator (LINAC), and biochemistry analyser. Currently, NMS' products are exported to over 60 countries and regions around the globe, serving more than 5,000 renowned customers. NMS' latest successful developments, such as the 128 Multi-Slice CT Scanner System, Superconducting MRI, LINAC, and PET products, have led China to become a global high-end medical equipment producer. As an integrated supplier with extensive experience in large medical equipment, NMS is committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described herein by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures may not be described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

As mentioned in the Background section above, in order to enhance the quality of CT images reconstructed based on the CT scan data set, the background generated due to a dark current of a CT detector's photodiodes, a bias current of integrators, and/or a noise that may exist during a data conversion process may be eliminated. That is to say, a background correction may be required for the CT scan data set. In an example, a background data set may be collected before a light source emits X-rays. A CT scan may then be performed to collect a CT scan data set. After the CT scan is completed, the collected background data set may be subtracted from the collected CT scan data set. However, during the CT scan process, the status (such as a temperature or a time, etc.) of the CT detector's components may change, which may further result in that the actual background may be changed. If these possible changes are ignored and the previously-collected background data set may be directly subtracted from the CT scan data set, ring artefacts may be introduced in the final CT image.

According to another example of the present disclosure, a first background data set may be collected before starting the CT scan and a second background data set may be collected after completing the CT scan. An interpolation operation may then be performed to obtain a corresponding background data set of the CT scan data set collected at any time during the CT scan process by using the first background data set and the second background data set in order to simulate changes to the background during the CT scan process, thereby improving the quality of reconstructed CT images.

Figure 1A:
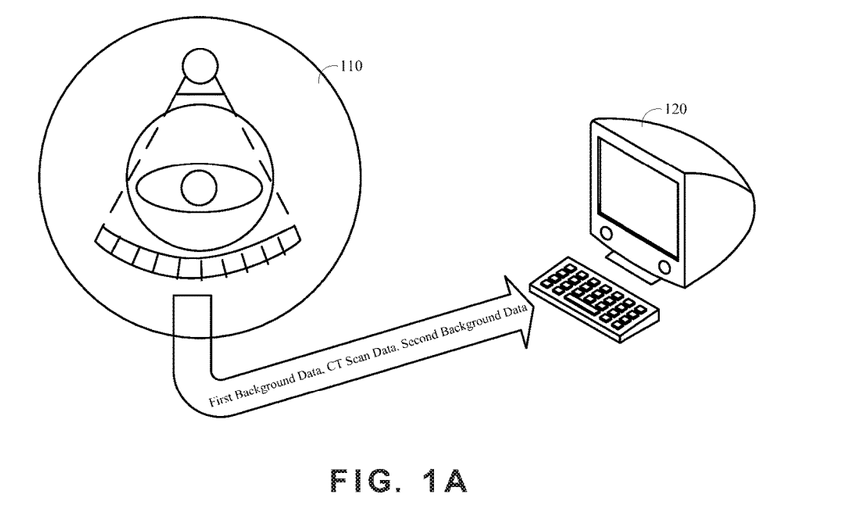
FIG. 1A is diagram of an operating system that adopts a background correction method for a CT scan data set according to an example of the present disclosure.
Figure 1B:
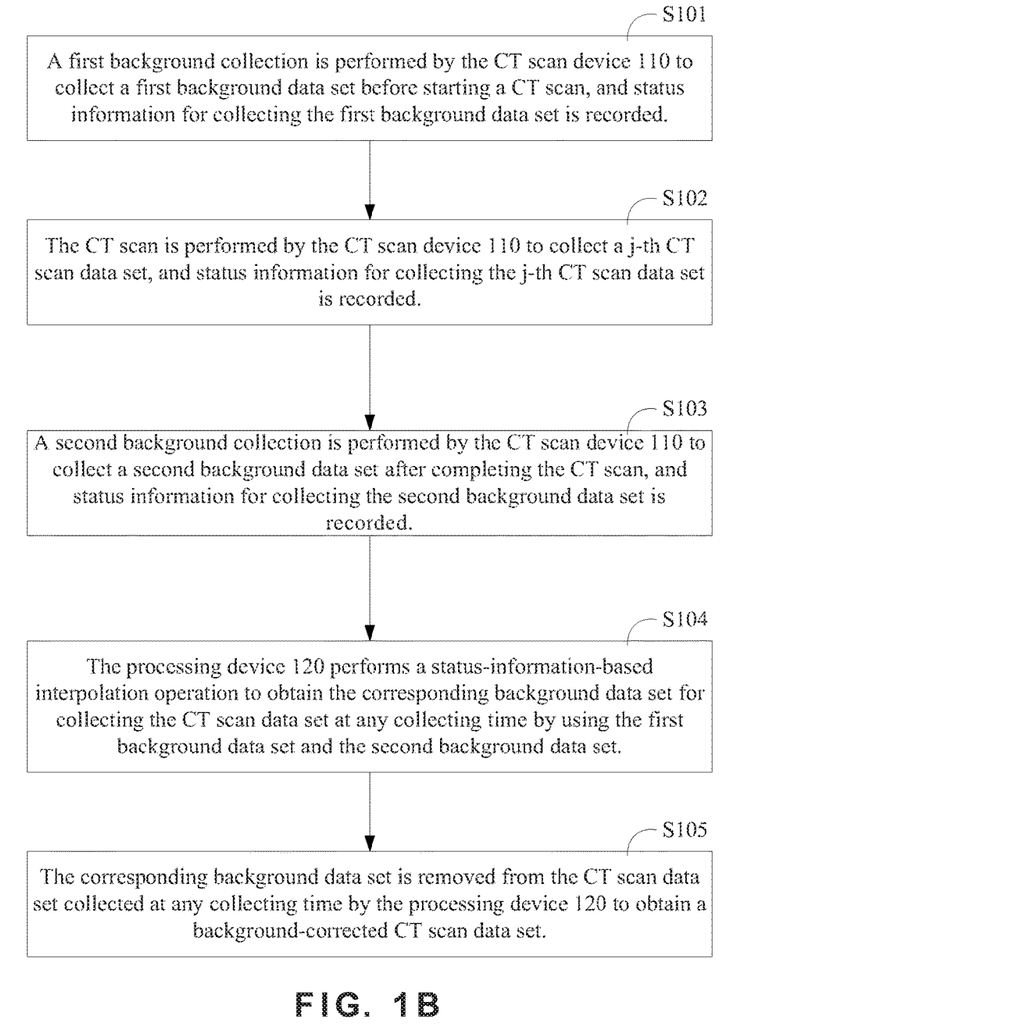
FIG. 1B is a flowchart illustrating the procedures of a background correction method for a CT scan data set according to an example of the present disclosure.

Referring to FIG. 1A. FIG. 1A provides a diagram of a CT system that adopts a background correction method for a CT scan data set according to an example of the present disclosure wherein the CT system may include a CT scan device 110 and a processing device 120 (such as a computer, etc.). Referring now to FIG. 1B, this figure shows a flowchart illustrating the procedures of a background correction method for a CT scan data set according to an example of the present disclosure.

At block S101, a first background collection may be performed by the CT scan device 110 to collect a first background data set DataBack 1 before starting a CT scan, and status information for collecting the first background data set DataBack 1 may be recorded. The status information may be information which makes the actual background change, such as a time $Time_{Back}^1$ or a temperature $Temp_{Back}^1$ (i) of a detector component.

During the process of performing the background collection, the light source may not emit X-rays, but the CT detector may still collect data.

In a particular example, i=1: N, wherein N represents a number of the detector components that recorded the temperature, and i represents an index number of the detector component. For example, if N=2, it may represent that a detector chip temperature Temp(1) and a detector chamber temperature Temp(2) are recorded.

At block S102, the CT scan may be performed by the CT scan device 110 to collect a j-th CT scan data set DataScan (j), and status information (such as, a time $\text{Time}_{Xray}^{j}$ and/or a temperature $\text{Temp}_{Xray}^{j}(i)$ of a detector component, etc.) for collecting the j-th CT scan data set DataScan(j) may be recorded.

During the CT scan process, the CT scan device 110 may perform the CT scan data collection process many times. For example, j=1: M, wherein M represents a total number of the CT scan data sets collected during the CT scan process, and j represents an index number of one of the CT scan data sets collected.

At block S103, a second background collection may be performed by the CT scan device 110 to collect a second background data set DataBack 2 after completing the CT scan, and status information (such as, a time $\text{Time}_{Back}^{2}$ and/or a temperature $\text{Temp}_{Back}^{2}(i)$ of a detector component, etc.) for collecting the second background data set DataBack 2 may be recorded.

At block S104, the processing device 120 performs a status-information-based interpolation operation to obtain the corresponding background data set DataBack(j) for collecting the CT scan data set DataScan(j) at any collecting time $\text{Time}_{Xray}^{j}$ by using the first background data set DataBack 1 and the second background data set DataBack 2.

In some examples, the interpolation operation may be a linear interpolation or a nonlinear interpolation.

In an example, a time-based linear interpolation operation may be performed to calculate the corresponding background data set DataBack(j) for collecting the j-th CT scan data set DataScan(j) at the j-th collecting time $\text{Time}_{Xray}^{j}$ by using the first background data set DataBack 1 and the second background data set DataBack 2. The specific operation may be shown according to the following formula:

$$DataBack(j) = \frac{Time_{Xray}^{j} - Time_{Back}^{1}}{Time_{Back}^{2} - Time_{Back}^{1}} * DataBack2 + \frac{Time_{Back}^{2} - Time_{Xray}^{j}}{Time_{Back}^{2} - Time_{Back}^{1}} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; $\text{Time}_{Xray}^{j}$ represents a time for collecting the j-th CT scan data set DataScan(j); DataBack 1 represents the first background data set; $\text{Time}_{Back}^{1}$ represents a time for collecting the first background data set DataBack 1; DataBack 2 represents the second background data set; and $\text{Time}_{Back}^{2}$ represents a time for collecting the second background data set DataBack 2.

In another example, a linear interpolation operation may be performed based on a temperature of an i-th detector component, and the specific operation may be shown according to the following formula:

$$DataBack(j) = \frac{Temp_{Xray}^{j}(i) - Temp_{Back}^{1}(i)}{Temp_{Back}^{2}(i) - Temp_{Back}^{1}(i)} * DataBack2 + \frac{Temp_{Back}^{2}(i) - Temp_{Xray}^{j}(i)}{Temp_{Back}^{2}(i) - Temp_{Back}^{1}(i)} * DataBack1.$$

As used herein, DataBack(j) represents the corresponding background data set for collecting the j-th CT scan data set DataScan(j) during the CT scan process, j=1 M, and M represents a number of the CT scan data sets collected during the CT scan process; $\text{Temp}_{Xray}^{j}(i)$ represents a temperature of an i-th detector component for collecting the j-th CT scan data set DataScan(j), i=1: N, and N represents a number of the detector components that recorded the temperature; DataBack 1 represents the first background data set; $\text{Temp}_{Back}^{1}(i)$ represents a temperature of the i-th detector component for collecting the first background data set DataBack 1; DataBack 2 represents the second background data set; and $\text{Temp}_{Back}^{2}(i)$ represents a temperature of the i-th detector component for collecting the second background data set DataBack 2.

In another example, a linear interpolation operation may be performed based on an average temperature of a plurality of detector components, and the specific operation may be shown according to the following formula:

$$DataBack(j) = \frac{AvTemp_{Xray}^{j} - AvTemp_{Back}^{1}}{AvTemp_{Back}^{2} - AvTemp_{Back}^{1}} * DataBack2 + \frac{AvTemp_{Back}^{2} - AvTemp_{Xray}^{j}}{AvTemp_{Back}^{2} - AvTemp_{Back}^{1}} * DataBack1.$$

As used herein, DataBack(j) represents the corresponding background data set for collecting the j-th CT scan data set DataScan(j) during the CT scan process, j=1 M, and M represents a number of the CT scan data sets collected during the CT scan process; $\text{AvTemp}_{Xray}^{j}$ represents an average temperature of a plurality of detector components for collecting the j-th CT scan data set DataScan(j), and the plurality of detector components may be a part of or all of the detector components that recorded the temperature; DataBack 1 represents the first background data set; $\text{AvTemp}_{Back}^{1}$ represents an average temperature of the plurality of detector components for collecting the first background data set DataBack 1; DataBack 2 represents the second background data set; and $\text{AvTemp}_{Back}^{2}$ represents an average temperature of the plurality of detector components for collecting the second background data set DataBack 2.

At block S105, the corresponding background data set DataBack(j) may be removed from the CT scan data set DataScan(j) collected at any collecting time $\text{Time}_{Xray}^{j}$ by the processing device 120 to obtain a background-corrected CT scan data set DataScan (j)$_{corrected}$ The specific operation may be shown according to the following formula:

$$DataScan(j)_{corrected} = DataScan(j) - DataBack(j).$$

Through collecting a first background data set before starting the CT scan and collecting a second background data set after completing the CT scan, and performing a interpolation operation to obtain a corresponding background data set of the CT scan data set collected at any time during the CT scan process by using the first background data set and the second background data set in order to simulate changes of the background during the CT scan process, the quality of reconstructed CT images may be enhanced.

Figure 2:
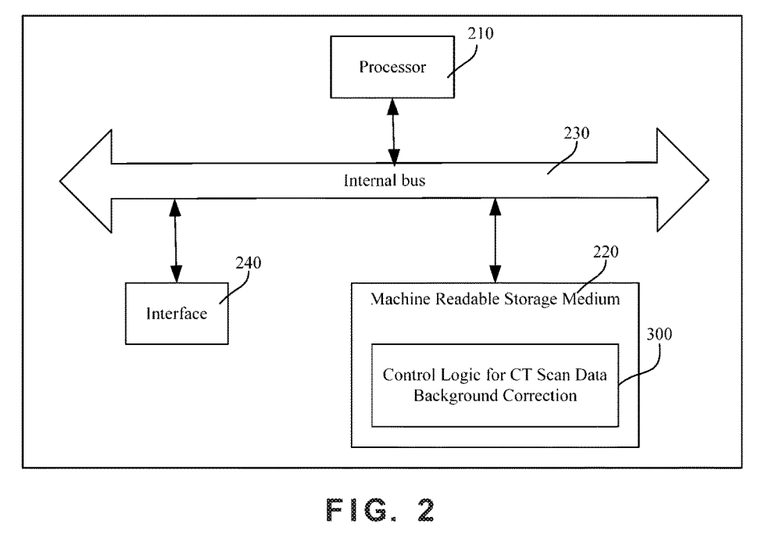
FIG. 2 is a hardware architecture diagram of a background correction device for CT scan data according to an example of the present disclosure.

In accordance with the above mentioned method, a background correction device for CT scan data may be provided in the present disclosure. Referring now to FIG. 2, FIG. 2 shows a hardware architecture diagram of a background correction device for CT scan data according to an example of the present disclosure. In an example, the background correction device for CT scan data may include a processor 210 and a machine readable storage medium 220, wherein the processor 210 may be connected to the machine readable storage medium 220 through an internal bus 230. In other possible implementations, the device may further include an interface 240 for communicating with other devices or components.

In different examples, the machine readable storage medium 220 may be Read Only Memory (ROM), non-volatile memory, flash memory, storage drives (such as, a hard drive), solid state drives, any type of storage disks (such as, CD-ROM, DVD, etc.), or similar storage mediums, or any combination thereof.

Figure 3:
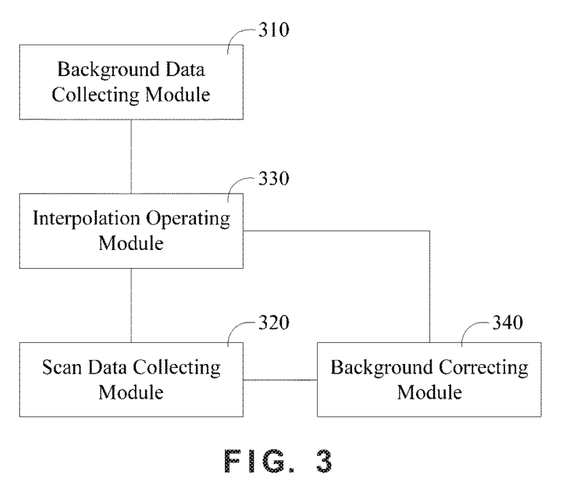
FIG. 3 is a block diagram of a control logic for a CT scan data set background correction according to an example of the present disclosure.

In an example, the machine readable storage medium 220 may be used for storing a control logic 300 for CT scan data set background correction. As shown in FIG. 3, a block diagram of the control logic 300 may further include a background data collecting module 310, a scan data collecting module 320, an interpolation operating module 330, and a background correcting module 340.

The background data collecting module 310 may be used for receiving a first background data set that a CT scan device may collect by performing a first background collection before starting a CT scan, and for recording status information (such as a time or a temperature of a detector component) indicating a status on which the CT scan device collected the first background data set. The background data collecting module 310 may further be used for receiving a second background data set that the CT scan device may collect by performing a second background collection after completing the CT scan, and for recording status information (such as a time or a temperature of a detector component) indicating a status on which the CT scan device collected the second background data set.

The scan data collecting module 320 may be used for receiving one or more CT scan data sets that the CT scan device may collect during the CT scan process, and for recording status information (such as a time or a temperature of a detector component) indicating a status on which the CT scan device collected each of the CT scan data sets.

The interpolation operating module 330 may be used for applying the first background data set, the second background data set, the corresponding status information of the first background data set, and the corresponding status information of the second background data set in order to obtain a corresponding background data set for collecting each of the CT scan data sets.

The background correcting module 340 may be used for removing the corresponding background data set from each of the CT scan data sets to obtain a background-corrected CT scan data set.

In an example, the interpolation operating module 330 may perform a time-based interpolation operation by using the first background data set and the second background data set. The time-based interpolation operation may be performed according to the following formula:

$$DataBack(j) = \frac{Time_{Xray}^j - Time_{Back}^1}{Time_{Back}^2 - Time_{Back}^1} * DataBack2 + \frac{Time_{Back}^2 - Time_{Xray}^j}{Time_{Back}^2 - Time_{Back}^1} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; $Time_{Xray}^j$ represents a time for collecting the j-th CT scan data set DataScan(j); DataBack 1 represents the first background data set; $Time_{Back}^1$ represents a time for collecting the first background data set DataBack 1; DataBack 2 represents the second background data set; and $Time_{Back}^2$ represents a time for collecting the second background data set DataBack 2.

In another example, the interpolation operating module 330 may perform a detector-component-temperature-based interpolation operation by using the first background data set and the second background data set. The detector-component-temperature-based interpolation operation may be performed according to the following formula:

$$DataBack(j) = \frac{Temp_{Xray}^j(i) - Temp_{Back}^1(i)}{Temp_{Back}^2(i) - Temp_{Back}^1(i)} * DataBack2 + \frac{Temp_{Back}^2(i) - Temp_{Xray}^j(i)}{Temp_{Back}^2(i) - Temp_{Back}^1(i)} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; $Temp_{Xray}^j(i)$ represents a temperature of an i-th detector component for collecting the j-th CT scan data set DataScan(j), i=1: N, and N represents a number of the detector components that recorded the temperature; DataBack 1 represents the first background data set; $Temp_{Back}^1(i)$ represents a temperature of the i-th detector component for collecting the first background data set DataBack 1; DataBack 2 represents the second background data set; and $Temp_{Back}^2(i)$ represents a temperature of the i-th detector component for collecting the second background data set DataBack 2.

In another example, the interpolation operating module 330 may perform a detector-component-temperature-based interpolation operation by using the first background data set and the second background data set. The detector-component-temperature-based interpolation operation may be performed according to the following formula:

$$DataBack(j) = \frac{AvTemp_{Xray}^j - AvTemp_{Back}^1}{AvTemp_{Back}^2 - AvTemp_{Back}^1} * DataBack2 + \frac{AvTemp_{Back}^2 - AvTemp_{Xray}^j}{AvTemp_{Back}^2 - AvTemp_{Back}^1} * DataBack1.$$

As used herein, DataBack(j) represents the corresponding background data set for collecting the j-th CT scan data set DataScan(j) during the CT scan process, j=1 M, and M represents a number of the CT scan data sets collected during the CT scan process; $AvTemp_{Xray}^j$ represents an average temperature of a plurality of detector components for collecting the j-th CT scan data set DataScan(j), and the plurality of detector components may be a part of or all of the detector components that recorded the temperature; DataBack 1 represents the first background data set; AvTemp$_{Back}^1$ represents an average temperature of the plurality of detector components for collecting the first background data set DataBack 1; DataBack 2 represents the second background data set; and AvTemp$_{Back}^2$ represents an average temperature of the plurality of detector components for collecting the second background data set DataBack 2.

In a further example, the background correcting module 340 may subtract the corresponding background data set from each of the CT scan data sets previously collected by using the first background data set and the second background data set according to the following formula:

DataScan(j)$_{corrected}$=DataScan(j)−DataBack(j).

As used herein, DataScan(j) represents a j-th CT scan data set collected during the CT scan process, j=1: M, and M represents a number of the CT scan data sets collected during the CT scan process; DataBack(j) represents the corresponding background data set for collecting the j-th CT scan data set DataScan(j) during the CT scan process; and DataScan (j)$_{corrected}$ represents a j-th background-corrected CT scan data set collected during the CT scan process.

The example below may be implemented with software, which describes how the background correction device for CT scan data may run the control logic 300. In this example, the control logic 300 of the present disclosure will be understood as machine readable instructions stored in the machine readable storage medium 220. When the processor 210 of the background correction device for CT scan data executes the control logic 300, the processor 210 may execute machine readable instructions of the control logic 300 that may be stored in the machine readable storage medium 220 to:

receive a first background data set that a CT scan device collected by performing a first background collection before starting a CT scan, and record status information (such as a time or a temperature of a detector component) indicating a status on which the CT scan device may collect the first background data set;

receive one or more CT scan data sets that the CT scan device may collect during the CT scan process, and record corresponding status information (such as, a time or a temperature of a detector component) indicating a status on which the CT scan device may collect each of the CT scan data sets;

receive a second background data set that the CT scan device may collect by performing a second background collection after completing the CT scan, and record status information (such as, a time or a temperature of a detector component) indicating a status on which the CT scan device may collect the second background data set;

use the first background data set, the second background data set, the corresponding status information of the first background data set, and the corresponding status information of the second background data set to obtain a corresponding background data set for collecting each of the CT scan data sets; and remove the corresponding background data set from each of the CT scan data sets to obtain a background-corrected CT scan data set.

In an example, a time-based interpolation operation may be performed by using the first background data set and the second background data set. The specific operation may be shown according to the following formula:

$$DataBack(j) = \frac{Time_{Xray}^j - Time_{Back}^1}{Time_{Back}^2 - Time_{Back}^1} * DataBack2 + \frac{Time_{Back}^2 - Time_{Xray}^j}{Time_{Back}^2 - Time_{Back}^1} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; Time$_{Xray}^j$ represents a time for collecting the j-th CT scan data set DataScan(j); DataBack 1 represents the first background data set; Time$_{Back}^1$ represents a time for collecting the first background data set DataBack 1; DataBack 2 represents the second background data set; and Time$_{Back}^2$ represents a time for collecting the second background data set DataBack 2.

In another example, a detector-component-temperature-based interpolation operation may be performed by using the first background data set and the second background data set. The specific operation may be shown according to the following formula:

$$DataBack(j) = \frac{Temp_{Xray}^j(i) - Temp_{Back}^1(i)}{Temp_{Back}^2(i) - Temp_{Back}^1(i)} * DataBack2 + \frac{Temp_{Back}^2(i) - Temp_{Xray}^j(i)}{Temp_{Back}^2(i) - Temp_{Back}^1(i)} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; Temp$_{Xray}^j$(i) represents a temperature of an i-th detector component for collecting the j-th CT scan data set DataScan(j), i=1: N, and N represents a number of the detector components that recorded the temperature; DataBack 1 represents the first background data set; Temp$_{Back}^1$(i) represents a temperature of the i-th detector component for collecting the first background data set DataBack 1; DataBack 2 represents the second background data set; and Temp$_{Back}^3$(i) represents a temperature of the i-th detector component for collecting the second background data set DataBack 2.

In another example, a detector-component-temperature-based interpolation operation may be performed by using the first background data set and the second background data set. The specific operation may be shown according to the following formula:

$$DataBack(j) = \frac{AvTemp_{Xray}^j - AvTemp_{Back}^1}{AvTemp_{Back}^2 - AvTemp_{Back}^1} * DataBack2 + \frac{AvTemp_{Back}^2 - AvTemp_{Xray}^j}{AvTemp_{Back}^2 - AvTemp_{Back}^1} * DataBack1.$$

As used herein, DataBack(j) represents the corresponding background data set for collecting the j-th CT scan data set DataScan(j) during the CT scan process, j=1: M, and M represents a number of the CT scan data sets collected during the CT scan process; $AvTemp_{Xray}^j$ represents an average temperature of a plurality of detector components for collecting the j-th CT scan data set DataScan(j), and the plurality of detector components may be a part of or all of the detector components that recorded the temperature; DataBack 1 represents the first background data set; $AvTemp_{Back}^1$ represents an average temperature of the plurality of detector components for collecting the first background data set DataBack 1; DataBack 2 represents the second background data set; and $AvTemp_{Back}^2$ represents an average temperature of the plurality of detector components for collecting the second background data set DataBack 2.

In an example, the corresponding background data set may be removed from each of the CT scan data sets according to the following formula:

$$DataScan(j)_{corrected} = DataScan(j) - DataBack(j).$$

As used herein, DataScan(j) represents a j-th CT scan data set collected during the CT scan process, j=1: M, and M represents a number of the CT scan data sets collected during the CT scan process; DataBack(j) represents the corresponding background data set for collecting the j-th CT scan data set DataScan(j) during the CT scan process; and DataScan (j)$_{corrected}$ represents a j-th background-corrected CT scan data set collected during the CT scan process.

The above are simply preferred examples of the present disclosure and is not intended to limit the disclosure within the spirit and principles of the present disclosure. Any changes made, equivalent replacement, or improvement in the protection of the present disclosure may be contained within the range of the present disclosure.

The methods, processes and units described herein may be implemented by hardware (including hardware logic circuitry), software or firmware and/or a combination thereof. The term "processor" is to be interpreted broadly to include a processing unit, ASIC, logic unit, and/or programmable gate array etc. The processes, methods and functional units may all be performed by the one or more processors; reference in this disclosure or the claims to a 'processor' may thus be interpreted to mean "one or more processors".

Further, the processes, methods and functional units described in this disclosure may be implemented in the form of a computer software product. The computer software product may be stored in a storage medium and may comprise a plurality of instructions for making a processor implement the methods recited in the examples of the present disclosure.

The figures are simply illustrations of an example, wherein the units or procedure shown in the figures are not necessarily essential for implementing the present disclosure. Those skilled in the art will understand that the units in the device in the example may be arranged in the device in the examples as described, or may be alternatively located in one or more devices different from that depicted in the examples. The units in the examples described may be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A background correction method for CT scan data, the method comprising:
    performing a first background collection to collect a first background data set before X-rays are emitted to start a CT scan, and recording status information corresponding to the first background data set, wherein the status information comprises a time;
    performing the CT scan to collect one or more CT scan data sets, and recording status information corresponding to each of the CT scan data sets;
    performing a second background collection to collect a second background data set after completing the CT scan when the X-rays are not emitted, and recording status information corresponding to the second background data set;
    performing a time-based interpolation operation to obtain a background data set corresponding to each of the collected CT scan data sets by using the first background data set and the second background data set, comprising:

$$DataBack(j) = \frac{Time_{Xray}^j - Time_{Back}^1}{Time_{Back}^2 - Time_{Back}^1} * DataBack2 + \frac{Time_{Back}^2 - Time_{Xray}^j}{Time_{Back}^2 - Time_{Back}^1} * DataBack1;$$

wherein DataBack(j) represents the background data set corresponding to a j-th CT scan data set DataScan(j) collected during the CT scan, j=1:M, and M represents a number of the CT scan data sets collected during the CT scan;
    $Time_{Xray}^j$ represents a time for collecting the j-th CT scan data set DataScan(j);
    DataBack 1 represents the first background data set;
    $Time_{Back}^1$ represents a time for collecting the first background data set DataBack 1;
    DataBack 2 represents the second background data set; and
    $Time_{Back}^2$ represents a time for collecting the second background data set DataBack 2; and
    removing the background data set corresponding to each of the collected CT scan data sets from each of the collected CT scan data sets to obtain a background-corrected CT scan data set.

2. The method according to claim 1, wherein said removing the background data set corresponding to each of the collected CT scan data sets from each of the collected CT scan data sets to obtain the background-corrected CT scan data set comprises:
    subtracting the background data set corresponding to each of the collected CT scan data sets from each of the collected CT scan data sets:

$$DataScan(j)_{corrected} = DataScan(j) - DataBack(j);$$

wherein DataScan(j) represents a j-th CT scan data set collected during the CT scan, j=1:M, and M represents a number of the CT scan data sets collected during the CT scan;

DataBack(j) represents the background data set corresponding to the j-th CT scan data set DataScan(j) collected during the CT scan; and DataScan(j)$_{corrected}$ represents a j-th background-corrected CT scan data set collected during the CT scan.

3. A background correction device for CT scan data, the device comprising:

a processor which invokes machine readable instructions corresponding to a control logic for CT scan data background correction stored on a storage medium and executes the machine readable instructions to perform the background correction method for CT scan data according to claim 1.

4. A background correction method for CT scan data, the method comprising:

performing a first background collection to collect a first background data set before X-rays are emitted to start a CT scan, and recording status information corresponding to the first background data set, wherein the status information comprises a temperature of a detector component;

performing the CT scan to collect one or more CT scan data sets, and recording status information corresponding to each of the CT scan data sets;

performing a second background collection to collect a second background data set after completing the CT scan when the X-rays are not emitted, and recording status information corresponding to the second background data set;

performing a detector-component-temperature-based interpolation operation to obtain a background data set corresponding to each of the collected CT scan data sets by using the first background data set and the second background data set, comprising:

$$DataBack(j) = \frac{Temp_{Xray}^{j}(i) - Temp_{Back}^{1}(i)}{Temp_{Back}^{2}(i) - Temp_{Back}^{1}(i)} * DataBack2 + \frac{Temp_{Back}^{2}(i) - Temp_{Xray}^{j}(i)}{Temp_{Back}^{2}(i) - Temp_{Back}^{1}(i)} * DataBack1;$$

wherein DataBack(j) represents the background data set corresponding to a j-th CT scan data set DataScan(j) collected during the CT scan, j=1:M, and M represents a number of the CT scan data sets collected during the CT scan;

Temp$_{Xray}^{j}$(i) represents a temperature of an i-th detector component for collecting the j-th CT scan data set DataScan(j), i=1:N, and N represents a number of the detector components that recorded the temperature;

DataBack 1 represents the first background data set;

Temp$_{back}^{1}$(i) represents a temperature of an i-th detector component for collecting the first background data set DataBack 1;

DataBack 2 represents the second background data set; and

Temp$_{Back}^{2}$(i) represents a temperature of an i-th detector component for collecting the second background data set DataBack 2; and removing the background data set corresponding to each of the collected CT scan data sets from each of the collected CT scan data sets to obtain a background-corrected CT scan data set.

5. A background correction device for CT scan data, the device comprising:

a processor which invokes machine readable instructions corresponding to a control logic for CT scan data background correction stored on a storage medium and executes the machine readable instructions to perform the background correction method for CT scan data according to claim 4.

6. A background correction method for CT scan data, the method comprising:

performing a first background collection to collect a first background data set before X-rays are emitted to start a CT scan, and recording status information corresponding to the first background data set, wherein the status information comprises a time and a temperature of a detector component;

performing the CT scan to collect one or more CT scan data sets, and recording status information corresponding to each of the CT scan data sets;

performing a second background collection to collect a second background data set after completing the CT scan when the X-rays are not emitted, and recording status information corresponding to the second background data set;

performing a detector-component-temperature-based interpolation operation to obtain a background data set corresponding to each of the collected CT scan data sets by using the first background data set and the second background data set, comprising:

$$DataBack(j) = \frac{AvTemp_{Xray}^{j} - AvTemp_{Back}^{1}}{AvTemp_{Back}^{2} - AvTemp_{Back}^{1}} * DataBack2 + \frac{AvTemp_{Back}^{2} - AvTemp_{Xray}^{j}}{AvTemp_{Back}^{2} - AvTemp_{Back}^{1}} * DataBack1;$$

wherein DataBack(j) represents the background data set corresponding to a j-th CT scan data set DataScan(j) collected during the CT scan, j=1:M, and M represents a number of the CT scan data sets collected during the CT scan;

AvTemp$_{Xray}^{j}$ represents an average temperature of a plurality of detector components for collecting the j-th CT scan data set DataScan(j);

DataBack 1 represents the first background data set;

AvTemp$_{Back}^{1}$ represents an average temperature of a plurality of detector components for collecting the first background data set DataBack 1;

DataBack 2 represents the second background data set; and

AvTemp$_{Back}^{2}$ represents an average temperature of a plurality of detector components for collecting the second background data set DataBack 2; and removing the background data set corresponding to each of the collected CT scan data sets from each of the collected CT scan data sets to obtain a background-corrected CT scan data set.

7. A background correction device for CT scan data, the device comprising:

a processor which invokes machine readable instructions corresponding to a control logic for CT scan data background correction stored on a storage medium and executes the machine readable instructions to perform the background correction method for CT scan data according to claim 6.

\* \* \* \* \*